United States Patent [19]

Goodfriend et al.

[11] Patent Number: 4,602,633
[45] Date of Patent: Jul. 29, 1986

[54] METHODS AND APPARATUS FOR DISINTEGRATION OF URINARY CALCULI UNDER DIRECT VISION

[75] Inventors: Roger Goodfriend, Santa Clara, Calif.; Clark E. Stohl, Jamestown, N.Y.

[73] Assignee: Blackstone Corporation, Jamestown, N.Y.

[21] Appl. No.: 672,118

[22] Filed: Nov. 16, 1984

[51] Int. Cl.⁴ .............................................. A61B 17/00
[52] U.S. Cl. ..................................................... 128/328
[58] Field of Search ............................... 128/328, 388

[56] References Cited

U.S. PATENT DOCUMENTS

| | | | |
|---|---|---|---|
| 3,352,303 | 12/1967 | Delaney | 128/24 |
| 3,927,675 | 12/1975 | Poolman | 128/328 |
| 4,243,040 | 1/1981 | Beecher | 128/328 |

FOREIGN PATENT DOCUMENTS

| | | | |
|---|---|---|---|
| 2604024 | 12/1976 | Fed. Rep. of Germany | 128/388 |
| 1487971 | 5/1971 | Japan . | |

OTHER PUBLICATIONS

Journal of Biomechanical Engineering–(79,80,81) May 1980.
"Ultrasonic and Electrohydraulic Lithotripsy of Ureteral Calculi", Urology, Jan. 1984, Roger Goodfriend, M.D.
"Disintegration of Ureteral Calculi by Ultrasound", by Roger Goodfriend, M.D., F.A.C.A., Urology, Mar., 1973.
Catalog entitled "Instruments for Stone-Surgery", Richard Wolf Medical Instrument Corporation, IV.83.
"A New Technique of Destroying Bladder Calculi: Litholapaxy", Der Urologe, Ausgabe A., Jan. 1971, K. H. Gasteyer.
"The Potential Use of Vibration for the Disintegration of Calculi", The Journal of Urology, Mar. 1957, Howard I. Suby.
"A Critical Appraisal of Methods for Disruption and Extraction of Urinary Calculi, Especially with Ultrasound", The Yale Journal of Biology and Medicine, Inc., 1955, Harold Lamport and Herbert Lamport and Herbert F. Newman.
Newspaper Article, Dec. 31, 1970, "Urinary Calculi Destroyed with Ultrasound": developed by K. H. Gasteyer and attached translation.

Primary Examiner—Gene Mancene
Assistant Examiner—Wenceslao J. Contreras
Attorney, Agent, or Firm—Buell Ziesenheim Beck & Alstadt

[57] ABSTRACT

A method and apparatus are provided for machining and disintegrating urinary calculi by subjecting the urinary calculi to ultrasonic forces transmitted by a wave guide in one passageway of a catheter while under observation through an optical system in a second parallel passage in the catheter.

10 Claims, 3 Drawing Figures

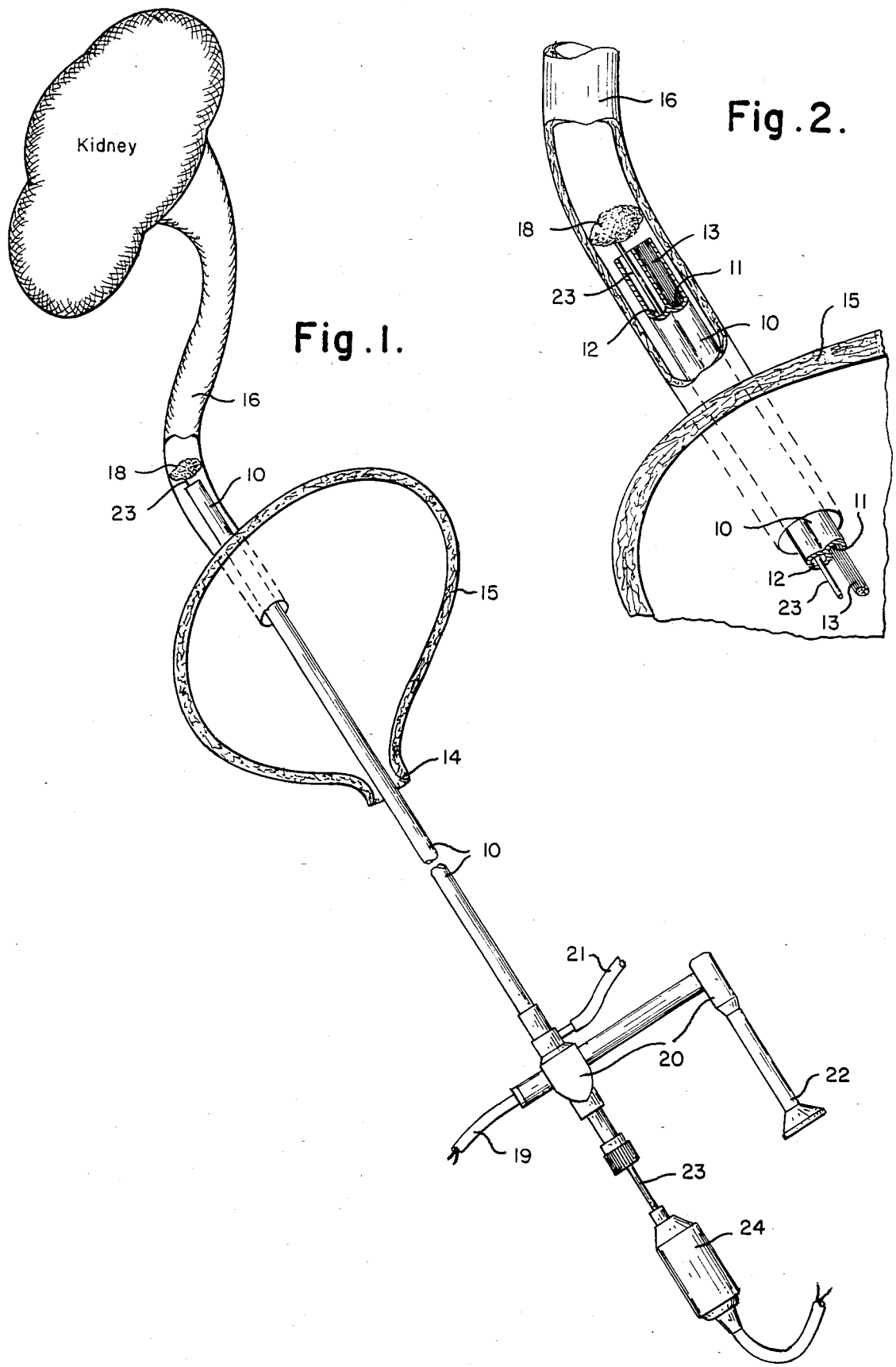

METHODS AND APPARATUS FOR DISINTEGRATION OF URINARY CALCULI UNDER DIRECT VISION

This invention relates to methods and apparatus for disintegration of urinary calculi under direct vision and particularly to such method and apparatus using ultrasonic apparatus jointly with direct visual observation of the disintegration of the urinary calculi.

The number of hospital admissions for removal of urinary calculi or stones averages about 0.1% of the population. This means that about a quarter million people or more per year are admitted in the United States for removal of kidney stones. In some cases where the stones are quite small, the stones may be passed without hospital care. However, larger stones and stones which are associated with obstruction or infection of the urinary tract must be removed to prevent damage. Historically, when the stone can be reached with mechanical devices and removed by manipulation this has been done, however, stones high in the ureter or held in the kidney were removed by open surgery.

In U.S. Pat. No. 3,830,240, Antonevich and Goodfriend proposed the use of an ultrasonic method and apparatus for removal of stones. The apparatus and method of that patent involved inserting a catheter carrying a coupling member through the ureter until it abutted the stone and then subjecting the coupling member to ultrasonic vibration with its free end against the stone to cause it to disintegrate the stone. A problem with this method and apparatus is that there is no direct visual observation of the stone during the disintegration step.

Prior to the inventions of Antonevich and Goodfriend the idea of vibratory impacting of urinary calculi in the bladder had been proposed. Machines using longitudinal vibrations through wire wave guides into the bladder had been tried but were too slow to be practical, difficult to control and created excessive heat.

The present invention solves these problems by providing an apparatus and method by means of which the kidney stone in the ureter would be machined into very small pieces under direct vision of the operator. This permits much faster disintegration and less chance of error and perforation of ureter in removal of the ureteral stones or stone.

We have discovered that ureteral stones can be quickly machined into small fragments under direct vision by placing a ureterscope which is essentially a two lumen catheter having at least a pair of side-by-side passages extending the length of the ureterscope into the ureter containing a stone to be removed with one end abutting the calculi, inserting a coupling member through one of the passageways of the catheter until one end abuts the stone while the other end extends outside the free end of the catheter, providing an optical system into another of the passageways of the catheter with an operative connection to an optical viewing means at the free end of the catheter, subjecting the coupling member to ultrasonic vibrations to produce longitudinal and transverse vibration at the end abutting the stone and moving the coupling member into the catheter to cause it to operate on the stone under direct vision through the viewing member through the optical system. Preferably, the optical system is a part of a ureterscope structure, however, the system could be based upon a fiber optics flexible system. An ultrasonic transducer is attached to the wave guide at its free end outside the catheter. The wave guide is preferably a wire. Preferably, the work or cutting area is irrigated or cooled by passing flushing fluid through the catheter around the wave guide in said one passageway or lumen.

In the foregoing general description of our invention we have set out certain objects, purposes and advantages of this invention. Other objects, purposes and advantages will be apparent from a consideration of the following description and the accompanying drawings in which:

FIG. 1 illustrates the apparatus of this invention in place in a human urinary tract and in place against a stone in a ureter;

FIG. 2 is an enlarged fragmentary view of the apparatus of FIG. 1 showing the catheter end at the kidney stone.

Figure 3:
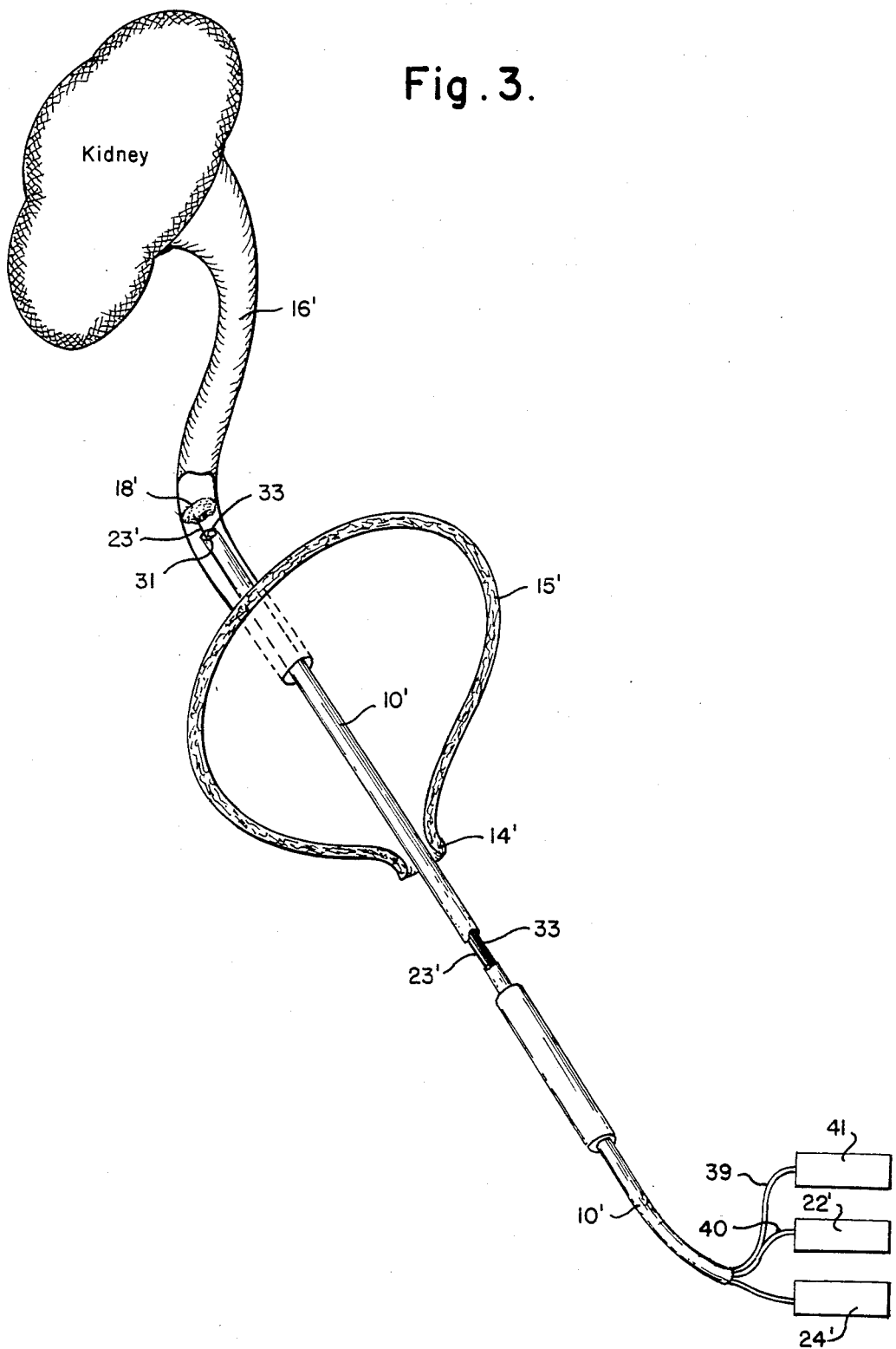
FIG. 3 is a second embodiment of apparatus according to this invention.

Referring to the drawings we have illustrated a catheter 10 having side-by-side generally parallel lumen or passageways 11 and 12 extending from one end to the other of the catheter. One lumen 11 carries an optical system 13 which extends from one end of the catheter which is inserted through the urethra 14 and bladder 15 of a patient, into the ureter 16 until it contacts stone 18 to be removed. The optical system 13 consists of a means of conducting light from a light source 19 to illuminate the stone 18 and a lens system 20 which is connected to a viewing means 22' through which the operating surgeon may view the area of the stone being machined. A wave guide or coupling member in the form of a wire 23 is inserted through the other lumen 12 of catheter 10 until one end contacts stone 18. The other end extends out of the free end of catheter 10 outside the body of the patient and is attached to a transducer 24 by any well known conventional means such as a set screw.

With one end of the catheter 10 and the wave guide 23 and optical system 13 in fixed position against the stone, the light source is activated and with the operator observing the work or machining area of the stone 18 the transducer 24 is activated to cause the wave guide 23 to act on the stone with transverse and longitudinal motion of the end of the wave guide to machine away or disintegrate the stone. A channel 21 is provided to lumen 12 to provide irrigation and cooling of the wave guide.

In the embodiments of FIG. 3 we have illustrated a similar system in which like parts from FIGS. 1 and 2 carry the same number with a prime sign. In this system, one lumen 31 carries a bundle of optical fibres 33 which extend from one end of the catheter to the other. One end of fibres 33 is adjacent the stone to be removed while the other end extends out the free end of catheter passageway 31 and is divided into two groups of fibres 39 and 40. One group 39 is attached to a light source 41 to illuminate the stone. The other group 40 is connected to viewing means 22' through which the surgeon may view the stone.

In the foregoing specification we have set out certain preferred practices and embodiments of our invention, however, the invention may be otherwise embodied within the scope of the following claims.

We claim:

1. An apparatus for machining and fragmenting urinary calculi in place in a ureter comprising a catheter adapted to be inserted into a ureter to abut a calculi to be removed, at least two substantially parallel passageways extending lengthwise of said catheter throughout its length and open at both ends, an optical system in one of said passageways permitting optical observation lengthwise through said catheter, a coupling member extending lengthwise through the other passageway of the catheter and having a diameter less than the interior diameter of said other passageway, ultrasonic means acting on the coupling member at one end to cause vibration at the other end, said optical system including a plurality of optical fibres forming an optical bundle and at least a part of said optical fibres being connected to a viewing means.

2. An apparatus as claimed in claim 1 wherein the optical fibres are divided into two groups, a light source connected to one end of one group and a viewing means connected to one end of the second group.

3. An apparatus as claimed in claim 1 or 2 wherein the coupling member is a wire.

4. An apparatus as claimed in claim 1 or 2 wherein the coupling member is a group of wires joined at the transducer end and spread out at the machining end.

5. A method of machining and fragmenting urinary calculi in place in a ureter comprising the steps of:
   (a) placing a catheter having at least two substantially parallel passageways extending lengthwise thereof and open at both ends in said ureter carrying the calculi to be removed with one end abutting said calculi;
   (b) placing an opitical system in one of said passageways with one end adjacent said calculi and the other end extending out of said passageway to permit optical viewing of said calculi at the end of said catheter, said optical system consisting of a plurality of optical fibres forming a bundle;
   (c) placing a coupling member in the other of said passageways in the catheter with one end of the coupling member abutting the calculi to be removed and the other end extending out of the opposite end of the passageway.
   (d) subjecting said coupling member to ultrasonic vibrations whereby the end of the coupling member abutting the calculi is caused to vibrate while being observed through the optical system in the said one of the passageway; and
   (e) moving said coupling member in the catheter under optical observation to cause the calculi to be machined and fragemented.

6. A method as claimed in claim 5 wherein the coupling member is caused to vibrate both longitudinally and transversely.

7. A method as claimed in claim 5 wherein the optical fibres are divided into two groups, attaching one group to a light source and illuminating the calculi thereby and attaching the other group to a viewing means and observing the calculi therethrough.

8. A method as claimed in claim 5 or 7 wherein th coupling member is a wire.

9. A method as claimed in claim 5 or 7 wherein flushing and irrigation fluid is introduced into the catheter whereby the catheter is irrigated with fluid during machining of the calculi.

10. A method as claimed in claim 8 wherein flushing and irrigation fluid is introduced into the catheter whereby the catheter is irrigated with fluid during machining of the calculi.

* * * * *

UNITED STATES PATENT AND TRADEMARK OFFICE
CERTIFICATE OF CORRECTION

PATENT NO.   : 4,602,633

DATED        : July 29, 1986

INVENTOR(S)  : ROGER GOODFRIEND, CLARK STOHL

It is certified that error appears in the above-identified patent and that said Letters Patent is hereby corrected as shown below:

The following prior art should be cited under the heading OTHER PUBLICATIONS:

Catalog entitled "Urology Catalog", American AMCI, 398-R2

Catalog entitled "A Breakthrough in Ultrasonic Lithotripsy, Karl Storz Endoscopy-America, Inc., Second Edition Column 4, claim 5, line 8, after passageway, remove "." and insert --;--.

Column 4, claim 8, line 25, change "th" to --the--.

Signed and Sealed this

Twenty-eighth Day of October, 1986

[SEAL]

Attest:

DONALD J. QUIGG

Attesting Officer      Commissioner of Patents and Trademarks